United States Patent [19]

Gardell et al.

[11] Patent Number: 4,628,026

[45] Date of Patent: Dec. 9, 1986

[54] METHOD AND APPARATUS FOR AUTOMATED DOUBLE FLUOROCHROMIZATION ANALYSIS IN LYMPHOCYTOTOXICITY TESTING

[76] Inventors: Dietlind Gardell, Box 38, Oxford Station, Ontario, K0G 1T0; Gail Rock, 270 Sandridge Road, Rockcliffe Park, Ottawa, Ontario, K1L 5A2, both of Canada

[21] Appl. No.: 552,090

[22] Filed: Nov. 15, 1983

[51] Int. Cl.[4] .................... G01N 33/53; G01N 33/554
[52] U.S. Cl. .................................. 435/7; 250/461.2; 435/29; 435/287; 436/519; 436/800; 436/805; 436/807; 436/808; 436/809; 436/821
[58] Field of Search .................... 435/29, 34, 7, 287; 436/519, 800, 805, 807, 809, 821; 250/461.2; 422/63, 65, 172; 424/11

[56] References Cited

U.S. PATENT DOCUMENTS

| | | | |
|---|---|---|---|
| 4,063,816 | 12/1977 | Itoi | 436/34 X |
| 4,100,416 | 7/1978 | Hirshfeld | 250/461.2 |
| 4,265,855 | 5/1981 | Mandle | 422/65 |
| 4,299,796 | 11/1981 | Esch | 422/63 |
| 4,314,026 | 2/1982 | Descamps-Latscha | 435/7 |
| 4,336,029 | 6/1982 | Natale | 436/172 |
| 4,354,114 | 10/1982 | Karnaukhov | 250/461.2 X |
| 4,471,056 | 9/1984 | Grumet | 424/11 X |
| 4,499,052 | 2/1985 | Fulwyler | 436/172 X |
| 4,532,203 | 7/1985 | Ullman | 435/7 |
| 4,554,839 | 11/1985 | Hewett | 422/65 X |
| 4,559,309 | 12/1985 | Evenson | 436/63 |
| 4,581,334 | 4/1986 | Kirchanski | 436/63 X |

OTHER PUBLICATIONS

Chemical Abstracts, 101:86887h (1984).
Abstract by Pablo Rubinstein, M.D. et al., entitled "Automated Reading of Cytotoxicity with the Contrast Fluorescence Test (CFT)", American Association for Clinical Histocompatibility Testing, Mar. 1981.
Rotman and Papermaster, (1966) Proc. N.A.S., pp. 134–141.
Edidin and Church, Transplantation, vol. 6, No. 9, pp. 1010–1014 (1968).
LePecq and Paoletti, J. Mol. Biol. (1967) 27, 87–106.
White, in Standardization in Immunofluorescence, Holborow Ed (1970).
Fong and Kissmeyer-Nielsen, Tissue Antigens (1972) 2.57–63.
Elves, Journal of Immunological Methods 2 (1972) 129–136.
Krisshan, The Journal of Cell Biology-vol. 66, 1975, pp. 188–193.
Goding, Journal of Immunological Methods, 13 (1976) 215–226.
Bruning, Kardol and Arentzen, Journal of Immunological Methods, 33 (1980) 33–44.

List Continued on next page.

Primary Examiner—Sidney Marantz

[57] ABSTRACT

An automated system for rapid sequential photometric analysis of a collection of double fluorochrome stained lymphocyte specimens, useful for antibody screening or lymphocytotoxicity analysis. The specimens are sequentially alternately irradiated with light of two distinguishable wavelengths, producing fluorescence at two distinguishable wavelengths. The fluorescent emission light intensity for each irradiation of each specimen is measured using a photometer and computer. The computer controls the synchronization of the irradiation through alternately selected condenser sets with the sequential movement of specimens into the optical path of the irradiating and detected light, and calculates the quotient of the light intensities emitted from each specimen at the two selected fluorescent light wavelengths. These quotients are compared against a control ratio (for lymphocytotoxicity analysis) to classify the specimen. Also described is a method of preparing specimens for such analysis, which requires that a complement be added to the first staining solution after the latter is applied to the specimens, then this combination agitated, and then the second staining solution added and the specimen incubated.

24 Claims, 7 Drawing Figures

OTHER PUBLICATIONS

Edidin, The Journal of Immunology, vol. 104, No. 5, May 1970.

Tagasugi, *Transplantation,* vol. 12, No. 2, (1971).

Martel, Jaramillo, Allen and Rubinstein, Vox Sang., 27: 13–20 (1974).

van Rood, van Leeuwen and Ploem, Nature, vol. 262, pp. 795–797 (1976).

Bruning, Claas, Kardol, Lansbergen, Naipal and Tanke, *Human Immunology,* 5, 225–231 (1982).

Johnson, Goddard and Holborow, Journal of Immunological Methods, 50 (1982) 277–280.

van Lambalgen, Bruning and Bradley, *Transplantation Proceedings,* vol. XV, No. 1, pp. 69–71 (1983).

Zeiss brochure, "IM 35 ICM 405 Photo-Invertoscopes".

Leitz brochure, "MPV Compact MT".

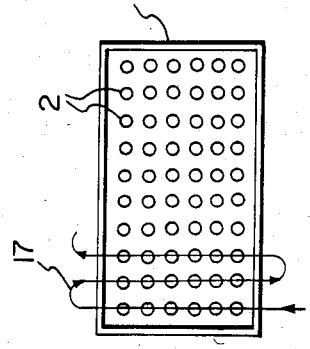
FIG.3
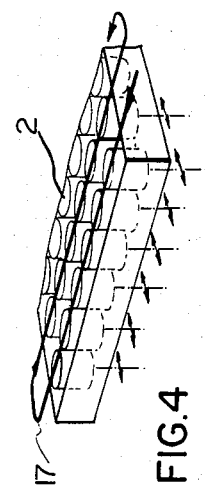
FIG.4
FIG.5
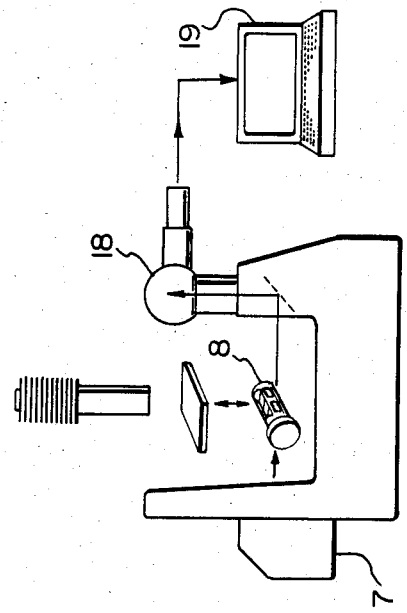
FIG.2

METHOD AND APPARATUS FOR AUTOMATED DOUBLE FLUOROCHROMIZATION ANALYSIS IN LYMPHOCYTOTOXICITY TESTING

FIELD OF THE INVENTION

This invention relates to an automated system for the rapid sequential photometric analysis of double fluorochrome stained cellular and non-cellular structures from the same selected object area of a specimen. With a plurality of specimens, fluorescence light intensities of different wavelengths emitted from a selected site in each specimen are quantitated in fast, sequential measuring steps.

More particularly, the invention relates to an automated method and apparatus for antibody screening, or for the testing of lymphocytotoxicity by double fluorochromization analysis which facilitates tissue typing procedures by providing objective standardized data, and to a method of preparing specimens for such testing.

The invention also relates to automated apparatus for observing fluorescence from a plurality of specimens each of which exhibits fluorescence at a first emission wavelength when irradiated with light of a first excitation wavelength and fluorescence at a second emission wavelength when irradiated with light of a second excitation wavelength, and to a method of preparing an automated lymphocytotoxicity assay simultaneously employing two contrasting fluorochromes.

DESCRIPTION OF THE PRIOR ART

The basic principles of immunofluorescence and their application in immunoenzyme analytical techniques are well known. Suitable fluorochromes, such as fluorescein (F) demonstrate the existence of biological structures, which are extra—or intracellular parts of cells or tissues, by creating fluorochromasia. Fluorescence reactions are observed with light of longer wavelength within the visible spectrum (green, yellow, orange or red) than that of the exciting light (green, blue or UV).

In 1966 Rotman and Papermaster (Biochemistry 55, 134-141, 1966) demonstrated that certain fluorescein esters of fatty acids, such as the diacetate FDA, used to stain cellular specimens, resulted in intracellular fluorescein retention due to hydrolysis of FDA to F, and highly intensive fluorochromasia.

As the degree of staining with FDA and like compounds depends directly, inter alia, on the integrity of the cell surface membrane, the intensity of fluorescence may be used in a visual differentiation of live and dead cells in a stained specimen. Methods of visualizing FDA stained live cells or of quantitating by measuring different fluorescence light intensities while simply assuming cell death and lysis in respect of the residual cellular material—described as monofluorochromatic assays—are unsatisfactory in that they only yield an estimate of the numbers of living and dead cells in a specimen, thereby failing to differentiate accurately between 100% killed (lysed) cells and merely absent cells.

In the NIH technique for testing lymphocytotoxicity the visual differentiation of live and dead cells is effected through the use the non-fluorescent stain eosin Y, which stains dead lymphocytes and not viable cells. Lymphocytes are added to the various typing sera in a microtyping tray, and the cell-serum mixtures incubated with rabbit complement. To each specimen the stain and buffered formaldehyde are sequentially added. Reactions of the cell-serum-complement-dye mixture are then read visually using a microscope, living lymphocytes appearing as small refractile bodies and dead reactive lymphocytes appearing as larger stained bodies or lysed cells. The reactions are evaluated by calculating the percentage of live cells in control negative and positive specimens and establishing whether or not a distinct increased staining (cell death) of lymphocytes occurs in the test specimens.

Both tests, the above-described cytotoxic test employing the uptake of a vital stain such as FDA and the NIH test, are slow (owing to the requirement for painstaking visual analysis of the specimens) and are sometimes subject to the inaccuracies inherent in assuming cell lysis in the absence of visible cells and to those arising from human error, e.g. the misreading of cells out of microscopic focus.

Reports that fluorochromes such as ethidium bromide (EB) (LePecq and Paoletti in Journal of Molecular Biology 27, 67-106, 1967), propidium iodide (PI) (Bruning et al, Human Immunology 5, 225-231, 1982), and rhodamine (R) (van Rood et al, Nature 262, 795-797, 1976) would form fluorescent complexes with nucleic acids resulting in luminescence within the red wavelength spectrum, suggested the possibility of "double-staining immunofluorescence (IF)" to differentiate between live and dead cells in a double stained specimen using well contrasting fluorochromization in an immune reaction. Dead cells can be selectively labelled with PI or EB, the stained dead cells fluorescing red in the presence of green and blue exciting light, respectively. The stain penetrates the membrane of damaged cells rapidly, where it gives a bright fluorescence with nuclear DNA.

The superiority of double staining IF with well contrasting images to the monofluorochromatic assays referred to above was demonstrated first by Edidin (J. Immunology 104-105, 1313-1315, 1970) and later by Tagasugi (Transplantation 12, 148-151, 1971). Edidin used the sequential application of contrasting stains, first differentiating live and dead cells by FDA fluorochromasia (Transplantation 6, 1010-1014, 1968) and later adding EB for spectrophotometrically assaying the dead cell IF in the lymphocytotoxicity assay.

Some efforts towards automation were reported by Martel, J. C. et al (Vox Sang 22, 13-20, 1974), using an FDA-EB double-staining technique, although automated data were not shown in their report. They too stressed the importance of actually measuring the numbers of living and dead cells rather than only estimating them as in the older FDA-monofluorochromatic assays.

In 1976, Van Rood et al employed a differential, double-staining technique to examine specimens of lymphocyte populations, including T and B cells. The cells were double-stained with FITC as a cell surface membrane marker for B cells and EB or R as a nuclear contrasting fluorochrome. The stained specimens were sequentially excited to obtain green IF from FITC-conjugated antiimmunoglobulins on B cells, contrasting with the red EB or R derived nuclear fluorochromasia. While future options for automation were discussed, none was shown in the reported results of Van Rood.

An attempt at achieving the highly desirable end of automation of standardized lymphocytotoxicity testing by microphotometry of double stained specimens was reported by Bruning et al (Human Immunology 5, 225-231, 1982). The cell specimens to be analyzed were held in Terasaki trays and studied with incident fluorescence light excitation using a Leitz MPV compact MT fitted with photomultiplier, motorized scanning stage, and a computer with printer unit. However, two separate staining methods had to be applied. A carboxyfluorescein fluorochromasia resulting in green fluorescence of live cells was used. In a separate staining procedure, the application of PI replaced the formaldehyde step of the NIH lymphocytotoxicity test after the complement-mediated lysis. The reported technique is not fully automated in that the microscopic equipment used did not allow for the fast sequential differentiation of one simultaneously dual-stained object, a procedure which is necessary for any fully automated typing technique.

SUMMARY OF THE INVENTION

Apparatus is provided according to the invention for use in fluorescence assays of specimens exhibiting fluorescence at two distinguishable wavelength bands when irradiated respectively by light of two pre-selected distinguishable wavelength bands. The apparatus comprises:

movable specimen containing means having spaced compartments for a plurality of individual specimens to be assayed;

alignment means for moving the container to provide sequential alignment of individual compartments of the container with an optical path;

irradiating means for irradiating said specimens sequentially and alternately with light of the two pre-selected distinguishable wavelength bands beamed along the optical path;

light collection means for receiving and distinguishing light produced by fluorescence in each said specimen along the optical path; and detector means for detecting and recording the intensity of the light produced by fluorescence of each said specimen at each of said two distinguishable wavelength bands.

The apparatus also preferably comprises a computer programmed to control and synchronize the operation of the alignment means, irradiating means, light collection means, and detector means. The computer preferably also includes quotient calculation means for calculating the quotients of the intensities of the light sequentially received from each said specimen at the two distinguishable wavelength bands; and comparison means for comparing the said quotient for each specimen against a predetermined control quotient thereby to classify the specimen according to such comparison.

The light collection means may include a pair of barrier filters each alternately selectable to pass light of a respective one of said two distinguishable wavelength bands to the detector means.

The movable specimen containing means may conveniently be a transparent specimen holder such as a microtiter tray containing the specimens in a planar array. The specimen holder may be movably retained in a conventional microscope including a scanning stage operable to retain said specimen holder and to be positioned to place any one of the specimens at a selected position within the objective field of said microscope, so as to collect for observation fluorescent radiation from said specimen. A conventional two-step motor can be provided which is operable to drive the scanning stage in orthogonal directions within a plane perpendicular to the focal axis of the objective of said microscope.

Two separate optical arrangements are selectably and alternately provided for each specimen. These arrangements are positioned to direct irradiating light of the two selected wavelength bands alternately in turn to each specimen (each specimen in turn being located at the selected position within the objective field of the microscope). These optical arrangements are also operable to transmit light of the selected emission wavelength bands, respectively, from each specimen in turn located at the selected position to the ocular of said microscope for observation or to a detector (e.g. a photomultiplier) which provides an output signal which can be utilized as an input to the computer.

A motor is provided for alternately positioning the first optical arrangement and the second optical arrangement in the path of light from the source of light. The computer or other suitable control means operatively connected with each of the motors causes the scanning stage to move in incremental steps, preferably in a meander path, to place each of the specimens sequentially at the selected position within the objective field of said microscope for a predetermined period of time. This actuates the optical arrangement selection motor during said predetermined period of time to position first one of the optical arrangements and then the other in the optical path from the specimen so that fluorescence light of the first emission wavelength and then of the second emission wavelength can be observed by means of the microscope for each of the specimens or can actuate the photomultiplier.

The two optical arrangements preferably comprise epi-fluorescence condenser sets. The motorized slide arrangement may comprise (i) a housing to hold the epi-fluorescence condenser sets in parallel side-by-side alignment (the housing being axially movable between two stop positions to alternately place said epi-fluorescence condenser sets in the path of light from said source), and (ii) a motor operatively connected to the housing for moving said housing between the two stop positions.

A method of preparing specimens for immunofluorescence measurement of the cytotoxic reaction between suitably prepared lymphocytes and selected identical quantities of antisera according to the invention comprises the sequential steps of:

(a) adding the lymphocytes (which have preferably been washed in a non-autofluorescing wash solution) to a first staining solution to prepare a suspension having a known concentration of lymphocytes, said first staining solution comprising a first fluorochrome selectively staining living cells, (b) adding a selected quantity of said suspension to each of said antisera and immediately thereafter adding to each of the antiserum-lymphocyte specimens a selected quantity of complement (C'), (c) agitating the specimens at room temperature for a selected period of time, (d) adding to each of the specimens a selected quantity of a second staining solution comprising a second fluorochrome selectively staining dead cells and exhibiting fluorescence over a range of wavelengths contrasting with the range of fluorescence exhibited by said first fluorochrome, and (e) incubating the specimens for a selected period of time.

A stabilizer may be added to the incubated specimens to inhibit further cytotoxic reaction between the antibodies of said antisera and the antigens of said lymphocytes, thereby decreasing background IF.

The first fluorochrome is preferably selected from the group consisting of fluorescein diacetate, fluorescein isothiocyanate and carboxyfluorescein diacetate, and the second stain is preferably selected from the group consisting of ethidium bromide, propidium iodide, rhodamine and rhodamine isothiocyanate (RITC).

The method according to the invention for fluorescence assays of specimens exhibiting fluorescence at two distinguishable wavelength bands when irradiated respectively by light of two pre-selected distinguishable wavelength bands comprises the following steps:
- sequentially aligning individual such specimens with an optical path;
- irradiating the specimens sequentially and alternately with light of the two pre-selected distinguishable wavelength bands beamed along the optical path;
- receiving and distinguishing light produced by fluorescence in each such specimen along the optical path; and
- detecting and recording the intensity of the light produced by fluorescence of each such specimen at each of said two distinguishable wavelength bands.

The automated method additionally comprises
- calculating the quotient of the intensities of the light sequentially received from each such specimen at the two distinguishable wavelength bands; and
- comparing the quotient for each specimen against a predetermined control quotient thereby to classify the specimen according to such comparison.

According to the fully automated system of double fluorochromization analysis in antibody screening or lymphocytotoxicity testing of the present invention, only one combined procedure is needed for the evaluation of live and dead cells stained with two contrasting fluorochromes. The controls are directly derived from the fluorescence light intensity (LI) raw data and expressed on a scale analogous to the percentage scale for cytotoxicity with percentages of live and dead cells. In a single evaluation step, both the negative and positive control quotients are simultaneously obtained from the same specimen object area. All results reflect directly transformed raw data and represent an interpretation of the double staining immunofluorescence measurement expressed as light intensities. The data analysis associated with the system includes a statistical validity check, any data exceeding three standard deviations off the mean being rejected and marked as such.

As a consequence of these features of the system of the invention, a considerable saving of time and manpower over prior techniques of analysis may be achieved while producing a quantitative assay using standardized procedures that are easily checked.

BRIEF DESCRIPTION OF THE DRAWINGS

In the drawings which illustrate embodiments of the invention:

FIG. 2 is a schematic view of a preferred embodiment of apparatus according to the invention.

FIGS. 3 and 4 are respectively a top plan view and a perspective view of a prepared microtest well tray showing by means of an arrow a preferred scanning sequence for the test wells when used in the automated scanning system of the invention.

FIG. 5 is a portion of a specimen computer print-out of the type obtained when the preferred automated embodiment and process of the invention are utilized.

DESCRIPTION OF PARTICULAR EMBODIMENT

As mentioned, the present invention is concerned with a rapid sequential photometric analysis of double fluorochrome stained cellular and non-cellular structures. If of cellular origin, the stained structures may be situated in the core, as in nuclear stains, or on the cell surface, as is the case when membrane markers are used.

Figure 1:
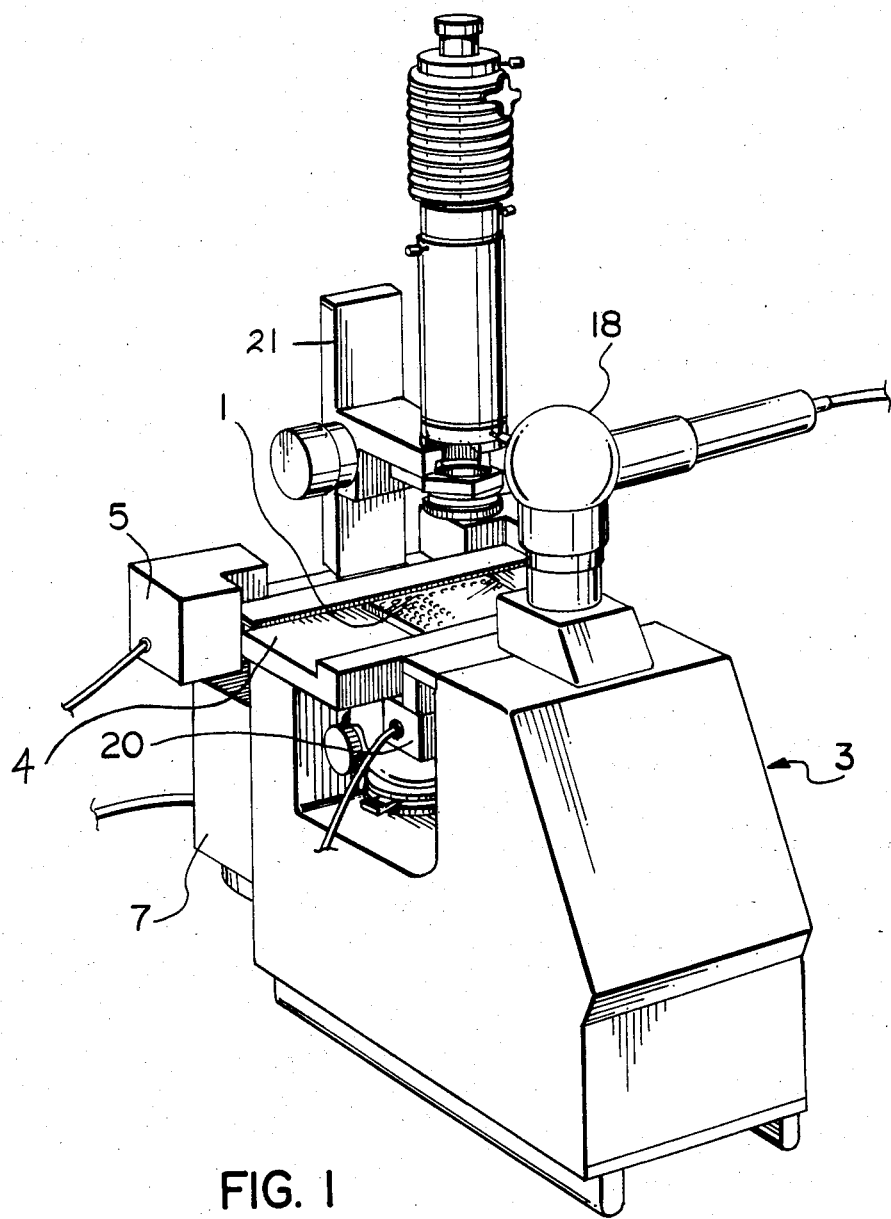
FIG. 1 is a perspective view of the modified epifluorescence invertoscope and related components employed in a preferred embodiment of apparatus according to the invention.

In the apparatus of the invention, any of a variety of standard trays and slides may be used to hold the stained cell culture specimens, e.g. microscope slides. However, microtiter trays of the kind illustrated as tray 1 in FIG. 1 are particularly well suited for use with the apparatus of the invention where the automated double-staining IF analysis of white blood cells is studied with incident fluorescent exciting light.

Tray 1 of FIGS. 2 and 3 contains sixty identical wells 2 for holding the specimens and standards to be analyzed. Automated antibody screening or lymphocytotoxicity testing with the system of the present invention is preferably performed in sixty or seventy-two well microtest trays.

In lymphocytotoxicity testing, target lymphocytes having an unknown antigenic pattern are reacted with selected quantities of antisera that have been placed in identified wells of the microtest tray. These antisera contain known antibodies and the IF data obtained by the method of the invention provide a measurement of cytotoxicity. Evaluation of cytotoxicity is employed in matching potential donors to a recipient in clinical immunology, e.g. tissue transplantation and blood transfusions where the known antisera may be those of the recipient and the target lymphocytes those of the potential donor.

In antibody screening, it is desired to identify the antibody specificity of unknown antisera. For example, it may be important to ascertain the antibodies present in the blood serum of a patient who has received a blood transfusion. Known quantities of the antisera are placed in the test wells of the microtest tray and are reacted with selected quantities of lymphocytes having a known antigenic pattern.

Whether the method of the invention used for lymphocytotoxicity testing, is employed for determining antigens or antibodies, the method of tray preparation is preferably as described below. However, in the former case commercially prepared standardized microtest trays containing the known antisera are available and may be used. In the latter case it is necessary first to add known quantities of the unknown antiserum or antisera to be tested to the microtest tray wells. In either case, the use of known quantities of antisera in reaction with known quantities of lymphocytes in the same quantitative relationship for each specimen testing is critical to obtaining reproducible quantitative measurements of cytotoxicity.

In the preparation of a specimen tray for lymphocytotoxicity according to the present invention, HLA antisera, including known negative and positive control sera are placed in the respective wells of non-autofluorescing microtiter trays. Viable target lymphocytes are washed in a medium which must contain no colourant capable of producing disturbing autofluorescence.

The target lymphocytes are then treated with a fluorochrome for later differentation between live cells and contrast-stained dead cells. The fluorochromization of dead cells occurs later following a specific antigen-antibody reaction. The live-stained cells are thoroughly washed to remove excess extracellular fluorochrome. Identical minute quantities of the singly-stained incubated cells are placed into selected wells of the tray wells. A selected portion of the tray wells contains equal quantities of positive and negative control standard antisera. These are known to be either reactive or non-reactive, respectively, with the lymphocyte cell surface membrane markers and serve as reference data in the computations conducted in the system of the present invention.

To the singly stained incubated cells, antisera and control standards, microquantities of complement are then added and the mixtures agitated in the wells of the microtest tray for a period of time which is sufficient for the antigen-antibody-complement interaction. Thereupon, to each of the cell samples and control standards a small quantity of a second staining agent is added. The reaction may be terminated by adding a stabilizer and centrifuging the trays.

The method of the invention is also applicable to antibody screening of unknown sera using lymphocytes having a known antigenic pattern. In that case, selected identical quantities of the sera to be tested are first placed in identified wells of the microtest tray. When choosing the two staining agents for the cells, it is preferable to use those fluorochromes which emit fluorescence light at different wavelengths, such as the well contrasting fluochromization in the green and yellow-orange-red ranges. Examples of dyes which fall within this definition are fluorescein-derived green fluorochromes, such as FITC, FDA, CFDA, on the one hand, or red fluorescent dyes such as EB, PI, R or RITC, on the other hand.

According to a preferred embodiment of the present invention, the automated evaluation of the prepared trays is performed using an inverted epi-fluorescence microscope which may be a conventional commercially available Zeiss* model IM 35 photo-invertoscope, modified as discussed in greater detail below.
* Trade Mark As seen in FIG. 1, the microscope indicated as 3 is provided with a scanning stage 4 adapted to hold microtest trays 1 and to be positioned to place any one of wells 2 at a fixed position pre-focused within the viewing field of the microscope objective. In the automated use of the system, as described below, scanning stage 4 is motorized to move in (say) 50 μm steps by X-Y drive motor 5. These components are individually known and readily commercially available.

Figure 7:
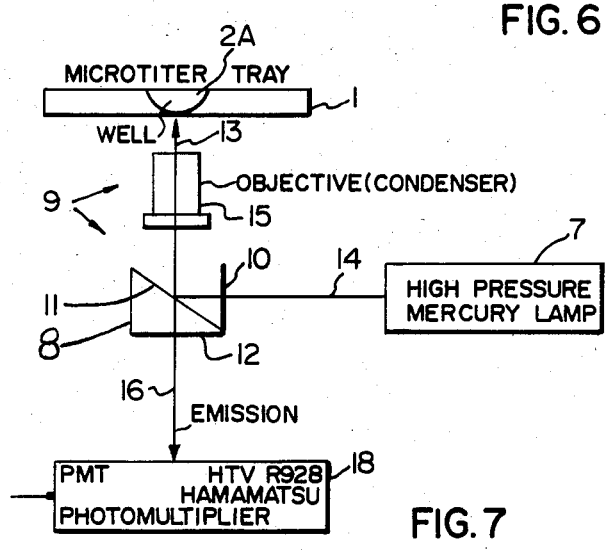
FIG. 7 is a schematic block diagram showing the optical path transversed by incident exciting light and by fluorescent radiation emanating from a sample being analyzed.

The arrangement of optical elements in microscope 3 is illustrated simply in FIGS. 2 and 7.

The source 7 of exciting radiation, is preferably an HBO 100 W high pressure mercury lamp which radiates over the visible wavelength spectrum. Light from the source may be selectively directed through a selected one of two epi-fluorescence condenser sets integrated into a single slideable dual condenser housing unit 8. In FIG. 7, elements of housing unit are shown with one of the condenser sets 9 in operating position. On the assumption that FDA is utilized (which will result in green immunofluorescence) and EB is selected as the contrasting stain (which will result in red immunofluorescence), then Zeiss* Models Nos. 48 77 10 and 48 77 15 may be used as the alternately selectable condenser sets.

Assume for the moment that the first of these condensers is positioned in the optical path illustrated in FIG. 7, Zeiss* condenser 48 77 10 comprises a blue exciter filter 10 (BP 450–490 nm), a chromatic beam splitter 11 for green fluorescence (FT 510 nm) and a barrier filter 12 (BP 520–560 nm) for green fluorescence.
* Trade Mark Light from the exciting source is filtered through exciter filter 10 and impinges at a 45° angle on beam splitter 11. The purpose of exciter filter 10 is to narrow the wavelength range of the light impinging on the specimens to approximately the blue range 450–490 nm suitable for excitation of specimens treated with FDA. The reflected portion of the blue light, indicated by arrow 13, is directed at right angles to the incident beam, indicated by line 14, and passes through fixed microscope objective 15, which focuses the blue exciting radiation onto the stained prepared specimen in well 2A of microtiter tray 1.

Back-scattered green fluorescence light, indicated by arrow 16, in turn passes through objective 15 and impinges on beam splitter 11. The transmitted portion of the green fluorescence is filtered through barrier filter 12, and passes through a pin hole with a diameter in the millimeter range onto the light-receiving aperture of photometer 18 (preferably an S'F photometer with Hamamatsu HTV R 928 photomultiplier tube) optically aligned with well 2A and objective 15 along an axis perpendicular to the beam of exciting light from light source 7. The transmitted fluorescence passing through barrier filter 12 may alternatively be observed visually through the ocular (not shown) of the microscope. The provision for direct visual microscopic examination of a specimen in a selected well within the viewing field of microscope objective 6 is not only to permit conventional visual specimen analysis when desired, but also to allow initial visual control of the centering of the test wells within the viewing field. The purpose of barrier filter 12 is to pass only the green light approximately in the band 520–560 nm which has been produced by fluorescein fluorochromasia.

As may be seen from FIG. 2, the movement of housing 8 at right angles to the plane defined by the optical pathways brings either selected one of the condenser sets into the operating position shown in the figure, only one condenser set at a time being placed in the optical path. The second condenser set is similarly constructed to the first, comprising an exciter filter, chromatic beam splitter and barrier filter, but operates to direct green light on the sample in the tray well and to pass to the photometer fluorescence in the red wavelength range. For this purpose, the second condenser set can be a Zeiss Model No. 48 77 15 with an exciter filter of BP 546-10, chromatic beam splitter FT 580, and barrier filter LP 590.

Housing 8 may be moved manually in the sense described above to alternately position the two condenser sets in the required optical path and to permit visual reading of the specimens through an eyepiece (e.g. the ocular of microscope 3) instead of taking photometric measurements of fluorescence intensity. In the automated system, housing 8 is actuated by a drive motor 20 in two stop movements for each sample measurement of green and red immunofluorescence, such drive motors being conventional and commercially available. In the automated process, the actual object measuring time of less than one second for each excitation wavelength does not result in any significant fading of fluorescence intensity. Accordingly, a single specimen can be read many times without loss of accuracy.

Earlier techniques of fluorochromization analysis employed transmitted light microscopy. The arrangement of an invertoscope with incident light fluorescence excitation, including a turn-back illumination carrier 21, has the advantages of providing a large working distance for use with all microtiter trays, and of a pre-focused selected position for a specimen in the objective field.

In automated operation, tray 1 is scanned by the motorized scanning stage so that each specimen or control well is successively brought into the focal position along the "meander" path indicated by the line 17 of FIGS. 3 and 4. For reproducibility of results, it is critical that each U-shaped well of the tray be successively very accurately centered at the pre-focused position within the optical field of the microscope objective. The meander path referred to above is best adapted to the requisite control of well positioning using an X-Y drive motor for the scanning stage holding the tray.

The automated system further includes computer assisted control means 19 (by way of example ZONAX* Intelligent Systems) for directing stepwise movement of X-Y drive motor 5 to center the specimens in the microtiter tray successively in a selected prefocused position of the microscope objective. The alternating motion of the movable filter housing is also synchronized under the control of the computer with the motion of the tray. The filter housing automatically successively interposes between the irradiated sample and the photometer the first barrier filter transparent to the green immunofluorescence light emanating from the FDA fluorochromasia and the second barrier filter transparent to the red immunofluorescence light emanating from the EB fluorochromasia, as previously described. The interface between control means 19 and drive motors 5 and 20 is conventional, and may comprise a buss connector and an analogue to digital converter.

* Trade Mark

Fluorescence light from each sample or control standard is measured as the output from photometer 18. The output is analyzed by the computer which also controls tray movement and switching of the filters. The computer-directed automatic measuring process uses the photomultiplied fluorescence light intensities as raw data and effects a computation resulting in quotients of arbitrary LI units derived from the two original IF measurements. The final human leukocyte antigen (HLA) score number represents a direct quotient transformation of the original dual staining IF data from the same object measuring field.

SPECIFIC EXAMPLE OF TRAY PREPARATION AND ANALYSIS RESULTS

In a preferred method of tray preparation for lymphocytotoxicity testing according to the invention, each well of a non-autofluorescing non-static microtiter tray is filled with 4 $\mu$l petrolatum (liquid) and 1 $\mu$l of HLA antiserum. Known negative and positive control sera are included. Lymphocytes are obtained from heparin blood by gradient centrifugation and three subsequent washes in phenol-red free Hank's balanced salt solution (HBSS), pH 7.2 to which 5% bovine serum albumin or fetal calf serum are added. Other washing solutions such as cell culture media may be used so long as their colour additives do not result in autofluorescence.

1 ml HBSS is added to a 10 $\mu$l aliquot of a FDA/acetone $-20°$ C. stock solution. The concentration of this stock solution may be in the range of 3-6 mg FDA per ml of acetone, but preferably 5 mg FDA/ml acetone. 100 $\mu$l of the FDA/acetone/HBSS mixture per $1.5-3 \times 10^6$, preferably $2 \times 10^6$ washed cells are incubated for up to 5 minutes, preferably for 4 minutes, then washed twice, 100 times diluted, in HBSS/BSA for 5 minutes at 2000 g, and adjusted to $2 \times 10^3$ cells/$\mu$l. 1 $\mu$l of the suspension is dropped into each well. 1-2 $\mu$l of complement (C') are added after a minimum of 30 minutes incubation time. The use of freeze-dried rabbit C', immediately prepared before use is recommended, as are equal amounts of fresh C'. More preferably, 1 $\mu$l of C' is combined immediately with the nuclear stained cells and continuously agitated at room temperature. The speed of the agitation may range from 10-50 cycles per minute and the corresponding range of time of agitation from 30-80 min. Preferably, the mixtures of antiserum, singly stained cells and C' are rotatively agitated at 30 rpm for 45 minutes. A 0.2-0.8 $\mu$l drop of ethidium bromide from an EB stock solution of 50 $\mu$g EB per 50 ml Veronal buffer, pH 7.0 is then added to each well and incubated for 7-15 minutes, preferably about 12 minutes. 1 $\mu$l of an disodium ethylene diamene tetraacetate/sodium chloride (EDTA-NaCl) solution of concentration in the range 0.2-1.2%, preferably 0.4%, may be added and the tray is rotated in a centrifugal movement at 200 g for 2-8 minutes, preferably about 3 minutes. The prepared tray is closed with its lid. No slide and/or oil is used to cover the test wells. The tray is then to be kept at 4° C. and may be read up to 24 hours after an initial period of "settling down" of the cells. The reading may be performed at room temperature with or without tray lid. However, trays should be stored at 4° immediately after reading.

Figure 6:
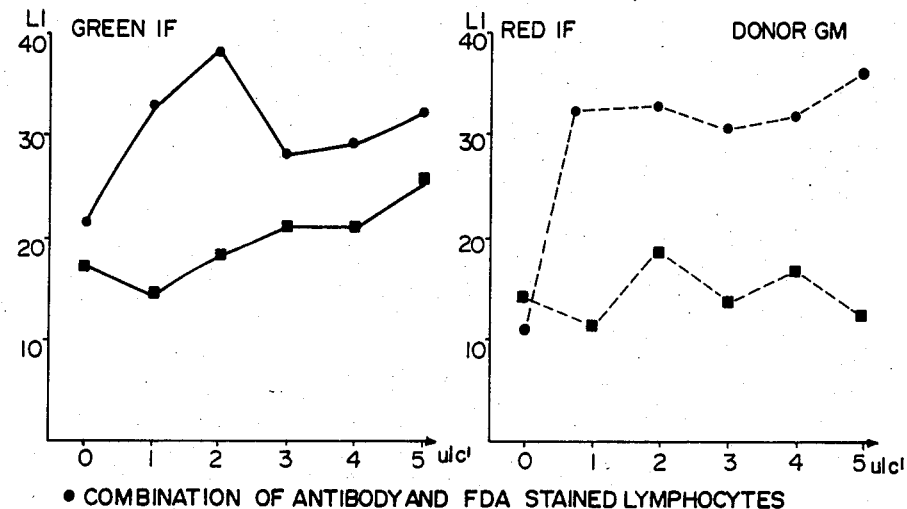
FIG. 6 comprises two graphic representations of immunofluorescence intensity measurements obtained using the apparatus of the invention in conjunction with the tray preparation method of the invention in connection with a specific example discussed below, in comparison with results obtained by utilizing a conventional technique.

FIG. 6 presents graphical representations of the green and red IF intensities, respectively, measured using the above-described apparatus and method of the invention for lymphocytotoxicity testing of target lymphocytes against standard antisera containing known antibodies. In each of the figures, the Y-coordinate represents the fluorescence intensity in arbitrary LI units. Each data point represents the average of ten to twelve calculated mean intensities, each of which is in turn the calculated average of fifteen original intensity measurements employing a damping factor of 15.

In FIG. 6 (both graphs), the X-coordinate is a measure in $\mu$l of the varying amounts of complement C' used in the test system. The circular data points were obtained by adding C' to the test wells immediately after addition of the FDA-stained cells to the antisera and slight agitation of the mixture. The square data points represent results obtained by the conventional procedure of incubating FDA-stained cells with the antisera for about 30 minutes prior to adding C'. It may be seen from the figures that the preferred method of tray preparation according to the invention gives rise to higher fluorescence light intensities than are conventionally obtained, with attendant decrease in percentage error of measurements.

The raw IF data and HLA scores for lymphocytotoxicity testing as presented by the ZONAX computer programmed according to the system of the present invention is illustrated below in a reproduction of a typical printer display (see also FIG. 5):

PLATE NUMBER: 101
PLATE NAME: R. Richards

|     | A     | B     | C     | D     | E     | F     |
| --- | ----- | ----- | ----- | ----- | ----- | ----- |
| 1:  | 184.6 | 143.5 | 214.3 | 145.2 | 272.1 | 129.4 |
| :   | 65.5  | 74.9  | 64.3  | 48.2  | 63.6  | 62.7  |
| 2:  | 204.5 | 255.0 | 216.9 | 192.6 | 177.7 | 223.6 |
| :   | 50.0  | 67.5  | 44.5  | 44.9  | 45.1  | 59.6  |
| 3:  | 161.7 | 208.7 | 218.3 | 161.7 | 157.3 | 157.4 |
| :   | 80.8  | 59.9  | 112.9 | 92.7  | 77.7  | 68.1  |
| 4:  | 175.2 | 141.5 | 140.3 | 150.1 | 158.5 | 182.3 |
| :   | 45.1  | 42.9  | 43.3  | 44.1  | 43.3  | 65.2  |
| 5:  | 150.5 | 161.7 | 177.8 | 159.1 | 174.6 | 226.5 |
| :   | 76.3  | 59.1  | 59.9  | 62.0  | 62.9  | 97.9  |
| 6:  | 124.5 | 125.5 | 133.1 | 143.9 | 126.6 | 149.2 |
| :   | 75.2  | 82.5  | 62.0  | 63.4  | 60.4  | 61.2  |
| 7:  | 147.4 | 207.1 | 188.5 | 176.1 | 175.9 | 166.8 |
| :   | 46.9  | 64.8  | 53.7  | 48.6  | 45.1  | 44.0  |
| 8:  | 135.8 | 127.4 | 143.9 | 142.5 | 158.1 | 143.3 |
| :   | 77.3  | 62.9  | 80.7  | 80.3  | 81.4  | 96.2  |
| 9:  | 193.3 | 194.0 | 207.2 | 236.9 | 177.1 | 190.8 |
| :   | 61.8  | 67.1  | 63.6  | 65.9  | 51.3  | 50.9  |
| 10: | 154.3 | 256.2 | 158.8 | 157.4 | 247.7 | 157.9 |
| :   | 83.1  | 89.7  | 77.0  | 81.7  | 61.5  | 87.3  |
| 1:  | 2.818 | 1.916 | 3.333 | 3.012 | 4.278 | 2.064 |
| 2:  | 4.090 | 3.778 | 4.874 | 4.290 | 3.940 | 3.752 |
| 3:  | 2.001 | 3.484 | 1.934 | 1.744 | 2.024 | 2.311 |
| 4:  | 3.885 | 3.298 | 3.240 | 3.404 | 3.661 | 2.796 |
| 5:  | 1.972 | 2.736 | 2.968 | 2.566 | 2.776 | 2.314 |
| 6:  | 1.656 | 1.521 | 2.147 | 2.270 | 2.096 | 2.438 |
| 7:  | 3.143 | 3.196 | 3.510 | 3.623 | 3.900 | 3.791 |
| 8:  | 1.757 | 2.025 | 1.783 | 1.775 | 1.942 | 1.490 |
| 9:  | 3.128 | 2.891 | 3.266 | 3.595 | 3.452 | 3.749 |
| 10: | 1.857 | 2.856 | 2.062 | 1.927 | 4.028 | 1.809 |
| 1:  | 1     | 8     | 1     | 1     | 1     | 8     |
| 2:  | 1     | 1     | 1     | 1     | 1     | 1     |
| 3:  | 8     | 1     | 8     | 8     | 8     | 4     |
| 4:  | 1     | 1     | 1     | 1     | 1     | 1     |
| 5:  | 8     | 1     | 1     | 2     | 1     | 4     |
| 6:  | 8     | 8     | 6     | 6     | 8     | 4     |
| 7:  | 1     | 1     | 1     | 1     | 1     | 1     |
| 8:  | 8     | 8     | 8     | 8     | 8     | 8     |
| 9:  | 1     | 1     | 1     | 1     | 1     | 1     |
| 10: | 8     | 1     | 8     | 8     | 1     | 8     |

In obtaining the above data, a single Falcon sixty-well plate was processed containing specimens identified by numerals 1 to 10 in the leftmost column of each printed table of data and the six letters A–F across the top of each table.

In the first table of data, the raw IF intensity data are given in arbitrary LI units, red IF above and green IF below. For example, specimen 8C produced red IF of 143.9 units and green IF of 80.7. Well 1A of the tray shows the negative control readings (viable cells), well 1B the positive control readings (dead cells) obtained by the same automated photometric action.

The second table of data presents red IF/green IF quotients and the third table HLA scores expressing the percentages of live and dead cells as integers from 1 to 8, each integer representing a selected range of cytotoxicity comparable to the percentage scale 0–100% derived from the standard NIH technique. Thus the HLA score of 1 for negative control 1A refers to cytotoxicity lying in the range 0–20% and the HLA score of 8 for positive control 1B refers to cytotoxicity in the range 81–100%. However, the automated LI measurements require an open scale due to the possibility of further increased green and red fluorescence intensities beyond those evaluated in the negative and positive control wells.

The program governing the system computer through the entire analysis procedure enables for the first time a completely automated tray analysis. Once the first well is centered in the object field and the system is set running, no further manual interference is needed for the evaluation of a prepared microtiter tray.

Functionally, the program includes a number of sub-programs, namely:

1. A plate measuring sub-program to determine the requisite accurate measuring steps for correct centering of tray wells to avoid deviations during tray evaluations. This sub-program permits the use in the system of different tray sizes and allows for dimensional variations between the multiple-well trays of different manufacturers and different lots of the same manufacturer. Further, the program permits the measurement of preselected areas of a tray in a single scan, instead of a complete scan through all tray wells.

2. A data acquisition sub-program. This includes parameters for identifying particular test trays, for controlling light source parameters such as high voltage and gain, damping factor, for controlling the motorized filter housing, including the sequence of fluorescence measurements, for controlling the motorized microscope stage and centering a well system within the focus of the microscope objective, routines for the measurement of photomultiplied IF and for the direct presentation of numerical LI data on the computer terminal screen.

3. A data analysis program which includes and prints pairs of raw green and red IF data, performs statistical evaluations and rejection of unacceptable data, transforms data into quotients, establishes a control range from highest and lowest absolute quotients, checks the actual negative and positive control well data with respect to their validity (rejecting them in the case of an unacceptable control range and replacing them with the highest and lowest measuring data), rearranges the control range according to the percentage range for lymphocytotoxicity, and provides for the arbitrary choice of a nomenclature for expressing the light intensity ranges of live and dead cells.

4. An antibody name program which provides for the co-ordination between serum and cell identification (name) in each tray well and IF measurement results, expressed as percentage of live over dead cells.

By means of control of the system through this program, each tray, regardless of size, number of sera, serum frequency within a tray or manufacturer of the tray may be correctly assayed. All results reflect directly transformed raw data and represent an interpretation of the double staining IF measurement expressed as light intensities. It is apparent that a number of alternative sets of program instructions might be employed in conjunction with the apparatus of this invention to effect the controls and measurements described above. Included as Appendix A to this disclosure is a listing of the plate measuring and data acquisition programs used by the applicants in conjunction with the ZONAX unit. Included as Appendix B is a listing of the data analysis program.

While a particular embodiment of applicants' invention has been described and shown with reference specifically to fully automated double fluorochromization analysis in lymphocytotoxicity testing, it is to be understood that this embodiment is illustrative only, and that the present invention is not limited thereto, but includes all embodiments falling within the scope of the appended claims.

APPENDIX A

```
1
2      C   ***********************************************************
3      C   *                                                         *
4      C   *      PROGRAM NAME :    FACT                             *
5      C   *                                                         *
6      C   *      LANGUAGE: FORTRAN 66                               *
7      C   *                                                         *
8      C   ***********************************************************
9      C   *                                                         *
10     C   *   VARIABLES :                                           *
11     C   *   ----------                                            *
12     C   *                                                         *
13     C   *   NOP    - INTEGER - NUMBER OF PLATES TO BE TYPED       *
14     C   *   X      - INTEGER - LOOP INDEX                         *
15     C   *   PNAME  - INTEGER - 30 BY 15 ARRAY OF PLATE NAMES      *
16     C   *   PNUM   - INTEGER - INDEX INTO PNAME ARRAY             *
17     C   *   WDIST  - REAL    - WELL DISTANCE                      *
18     C   *                    - DISTANCE BETWEEN WELLS (MM)        *
19     C   *   YMAX   - INTEGER - NUMBER OF WELLS IN THE X AND       *
20     C   *   XMAX             - Y DIRECTIONS                       *
21     C   *   PDATA  - REAL    - PLATE DATA                         *
22     C   *                    - REAL ARRAY 15 X 10 X 2             *
23     C   *                    - STORES PHOTOMETER READINGS         *
24     C   *                    - FOR EACH WELL (INDEXED BY X,Y)     *
25     C   *   X,Y    - INTEGER - INDEXES PLATE WELLS IN PDATA       *
26     C   *                    - AND FOR SCANNING                   *
27     C   *   GAVG   - REAL    - AVG PMT READING (GREEN FILT)       *
28     C   *   RAVG   - REAL    - AVG PMT READING (RED FILT)         *
29     C   *   FILTER - INTEGER - SWITCH INDICATING WHICH FILTER     *
30     C   *                    - TO BE USED FIRST.  1 = RED         *
31     C   *                    -                    2 = GREEN       *
32     C   *   DFACT  - INTEGER - PHOTOMETER DAMPING FACTOR          *
33     C   *                    - RANGE 1-100 INCLUSIVE              *
34     C   *                                                         *
35     C   ***********************************************************
36     C
37     C
38         PROGRAM FACT1
39     C
40         INTEGER*1 NOP,PNUM,J,ANSWER,PTYPE
41         INTEGER*1 PNAME(30,30),FNAME(6),NOW
42         INTEGER*1 DATE(15),PASS(8),PW(8),OK
43         REAL      PDATA(12,10,2),GMAX,GMIN,RMAX,RMIN
44         INTEGER*1 MORE
45         INTEGER*1 DFACT,FILTER,GAIN
46         INTEGER*2 XMAX,YMAX
47         INTEGER*2 HV,M,WDIST(12,10,2),X,Y,Z
48         INTEGER*2 XDIST,YDIST
49         INTEGER*2 CODE(6),ONE,TWO,THREE,FOUR,FIVE,SIX
50         INTEGER*2 NUMBER
51         REAL      RAVG,GAVG
52     C
53         EQUIVALENCE (CODE(1),ONE),(CODE(2),TWO),(CODE(3),THREE)
54         EQUIVALENCE (CODE(4),FOUR),(CODE(5),FIVE),(CODE(6),SIX)
55     C
56         DATA   PTYPE,MORE/2*0/
57         DATA   X,XMAX/1,1/
58         DATA   Y,Z,YMAX/1,1,1/
59         DATA   DFACT,FILTER/15,0/
60         DATA   NOP,PNUM,J,ANSWER/4*0/
61         DATA   GAVG,RAVG/0.0,0.0/
62         DATA   HV,GAIN/570,2/
```

```
63          DATA    PDATA/240*0.0/
64          DATA    WDIST/240*0/
65          DATA    PNAME/900*' '/
66          DATA    FNAME /6*' '/
67          DATA    PW(1),PW(2),PW(3),PW(4)/'F',' ','A',' '/
68          DATA    PW(5),PW(6),PW(7),PW(8)/'C',' ','T',' '/
69          DATA    PASS /8*'X'/
70          DATA    OK /0/
71          DATA    CODE/6*0/
72          DATA    DATE /15*' '/
73   C
74   C              CODE SECURITY ?
75   C              PASSWORD ?
76   C
77   C      ****************************************
78   C      *   PROMPT FOR TODAY'S DATE            *
79   C      ****************************************
80   C
81          DO 9 J=1,31
82       9     WRITE (1,10)
83      10    FORMAT(/1H+)
84          WRITE (1,11)
85      11  FORMAT(' PLEASE ENTER TODAY''S DATE : ')
86          READ  (1,12) (DATE(J),J=1,15)
87      12  FORMAT(15A1)
88   C
89   C      ****************************************
90   C      *   PROMPT FOR THE NUMBER OF PLATES    *
91   C      ****************************************
92   C
93          DO 13 J=1,31
94      13    WRITE (1,10)
95          NOP = 0
96      25  IF((NOP.GE.1).AND.(NOP.LE.30))  GOTO 40
97            WRITE (1,30)
98      30    FORMAT(' PLEASE ENTER THE NUMBER'/
99         +         ' OF PLATES TO BE TYPED :   ')
100           READ (1,35) NOP
101     35    FORMAT(I2)
102           GOTO 25
103     40  CONTINUE
104  C
105  C      *****PROMPT*FOR*PLATE*NAMES*************
106  C      ****************************************
107  C
108         DO 44 J=1,31
109     44    WRITE (1,10)
110         WRITE (1,50)
111         WRITE (1,52)
112
113     50  FORMAT(///
114        +        ' PLEASE ENTER A NAME FOR EACH PLATE.'/)
115     52  FORMAT(' (30 CHARACTERS MAXIMUM)'//
116        +        ' PLATE NO.    PLATE NAME ')
117  C
118     60  DO 90 PNUM=1,NOP
119           WRITE (1,70) PNUM
120     70    FORMAT(/1H+,4X,I2,8X)
121           READ  (1,80) (PNAME(PNUM,J),J=1,30)
122     80    FORMAT(30A1)
123     90  CONTINUE
124  C
125  C
126  C
127  C
128  C
129  C
130  C
131  C      ****************************************
132  C      *   EDIT PLATE NAMES                   *
133  C      ****************************************
134  C
135         ANSWER = 1
136     95  IF(ANSWER.NE.1) GOTO 240
137  C
138  C
```

```
C     ************************************************
C     *  DISPLAY ALL PLATE IDENTIFICATIONS           *
C     ************************************************
C
      DO 97 J=1,31
  97     WRITE (1,10)
      WRITE (1,99)
  99  FORMAT(//' THESE PLATE NAMES HAVE BEEN ENTERED :'/)
C
      DO 110 PNUM=1,NOP
         WRITE (1,100) PNUM,(PNAME(PNUM,J),J=1,30)
 100     FORMAT(' * ',I2,' * ',30A1,' * ')
 110  CONTINUE
C
C     ************************************************
C     *  PROMPT FOR PLATE IDENTIFICATION CHANGES     *
C     ************************************************
C
      ANSWER = 0
 115  IF((ANSWER.EQ.1).OR.(ANSWER.EQ.2)) GOTO 135
         WRITE (1,120)
 120     FORMAT(//' DO YOU WISH TO CHANGE ANY PLATE NAMES ?',
     +          ' (Y OR N)    ')
C
         CALL OUT( 8,199 )
 124     CALL OUT( 7,6 )
         IF( INP(1).NE.251 )  GOTO 126
            ANSWER = 1
            GOTO 130
 126     CALL OUT( 7,1 )
         IF( INP(1).NE.253 )  GOTO 128
            ANSWER = 2
            GOTO 130
 128     GOTO 124
C
 130     CONTINUE
         CALL OUT( 8,207 )
         GOTO 115
 135  CONTINUE
C
C
C     ************************************************
C     *  LINES 140 THRU 240 - EDITING LOOP           *
C     ************************************************
C
      IF(ANSWER.NE.1) GOTO 230
         PNUM = 999
 140     IF(PNUM.EQ.0) GOTO 220
 150        IF(((PNUM.GE.1).AND.(PNUM.LE.NOP))
     +              .OR.(PNUM.EQ.0)) GOTO 180
               DO 154 J=1,31
 154              WRITE (1,10)
               WRITE (1,160)
 160           FORMAT(//' ENTER NUMBER OF PLATE WHOSE NAME IS TO BE'/
     +                ' CHANGED, OR "0" TO END NAME CHANGES         ')
               READ (1,170) PNUM
 170           FORMAT(I2)
               GOTO 150
 180        CONTINUE
C
            IF(PNUM.EQ.0) GOTO 210
               WRITE (1,190) (PNAME(PNUM,J),J=1,30)
 190           FORMAT('    OLD NAME',20X,'NEW NAME'/
     +                2X,30A1)
               READ (1,200) (PNAME(PNUM,J),J=1,30)
 200           FORMAT(30A1)
               PNUM = 999
 210        CONTINUE
            GOTO 140
 220     CONTINUE
 230  CONTINUE
      GOTO 95
 240  CONTINUE
C
C
C
```

```
215     C     ****************************************
216     C     *   PROMPT FOR SCANNING PARAMETERS     *
217     C     ****************************************
218     C
219           DO 242 J=1,31
220     242   WRITE (1,10)
221           PTYPE = 0
222     245 IF((PTYPE.GE.1).AND.(PTYPE.LE.4)) GOTO 300
223           WRITE (1,250)
224     250   FORMAT(//' PLEASE ENTER THE NUMBER OF THE PLATE '
225         +      /' BEING USED :      1. FALCON   60 WELL PLATE'/
226         +      '                    2. ROBBINS  72 WELL PLATE'/
227         +      '                    3. COOKE    96 WELL PLATE'/
228         +      '                    4. OTHER',15X)
229           CALL OUT( 8,199 )
230     255   CALL OUT( 7,14 )
231           IF( INP(1).NE.254 )  GOTO 260
232                PTYPE = 1
233                GOTO  295
234     260   CALL OUT( 7,13 )
235           IF( INP(1).NE.254 )  GOTO 270
236                PTYPE = 2
237                GOTO  295
238     270   CALL OUT( 7,12 )
239           IF( INP(1).NE.254 )  GOTO 280
240                PTYPE = 3
241                GOTO  295
242     280   CALL OUT( 7,11 )
243           IF( INP(1).NE.254 )  GOTO 290
244                PTYPE = 4
245                GOTO  295
246     290   GOTO 255
247     295   CONTINUE
248           CALL OUT( 8,207 )
249           GOTO 245
250     300 CONTINUE
251     C
252     C     ****************************************
253     C     *   READ IN PLATE MEASUREMENT DATA     *
254     C     ****************************************
255     C
256           GOTO (320,330,340,350),PTYPE
257     C
258     320 CALL OPEN( 7,'FALCON' )
259         READ  (7,321) (FNAME(J),J=1,6)
260     321 FORMAT(6A1)
261         READ  (7,322) NOW,XMAX,YMAX
262     322 FORMAT(3I3)
263         DO 328 X=1,XMAX
264           DO 326 Y=1,YMAX
265             READ  (7,324) WDIST(X,Y,1),WDIST(X,Y,2)
266     324     FORMAT(2I5)
267     326   CONTINUE
268     328 CONTINUE
269         GOTO 375
270     C
271     330 CALL OPEN( 7,'ROBBIN' )
272         READ  (7,331) (FNAME(J),J=1,6)
273     331 FORMAT(6A1)
274         READ  (7,332) NOW,XMAX,YMAX
275     332 FORMAT(3I3)
276         DO 338 X=1,XMAX
277           DO 336 Y=1,YMAX
278             READ  (7,334) WDIST(X,Y,1),WDIST(X,Y,2)
279     334     FORMAT(2I5)
280     336   CONTINUE
281     338 CONTINUE
282         GOTO 375
283     C
284     340 CALL OPEN( 7,'COOKE' )
285         READ  (7,341) (FNAME(J),J=1,6)
286     341 FORMAT(6A1)
287         READ  (7,342) NOW,XMAX,YMAX
288     342 FORMAT(3I3)
289         DO 348 X=1,XMAX
```

```
            DO 346 Y=1,YMAX
              READ  (7,344) WDIST(X,Y,1),WDIST(X,Y,2)
344     FORMAT(2I5)
346     CONTINUE
348 CONTINUE
        GOTO 375
C
350 DO 351 J=1,31
351     WRITE (1,10)
        WRITE (1,355)
355 FORMAT('    PLEASE ENTER THE NAME OF FILE CONTAINING'/
    +        '    THE PLATE MEASUREMENTS (6 CHRS MAX)   :   ')
        READ  (1,360)(FNAME(J),J=1,6)
360 FORMAT(6A1)
        CALL OPEN( 7,FNAME )
        READ  (7,362)(FNAME(J),J=1,6)
362 FORMAT(6A1)
        READ  (7,365) NOW,XMAX,YMAX
365 FORMAT(3I3)
        DO 372 X=1,XMAX
          DO 370 Y=1,YMAX
            READ  (7,368) WDIST(X,Y,1),WDIST(X,Y,2)
368     FORMAT(2I5)
370     CONTINUE
372 CONTINUE
C
375 CONTINUE
C
C   ***********************************************
C   *  SET HIGH VOLTAGE AND GAIN                  *
C   ***********************************************
C
        M = ((HV*255.0)/1200.0)
        CALL POKE( 23554,M )
        CALL POKE( 23555,GAIN )
C
C
C
C
C
C
        CALL OPEN( 8,'1:FACT.DAT' )
        WRITE (8,510) NOP,XMAX,YMAX,GAIN,FILTER,NOW,
    +                 (FNAME(J),J=1,6),HV,(DATE(K),K=1,15)
510     FORMAT(6I3,6A1,I4,15A1)
C   ***********************************************
C   *  PLATE PROCESSING LOOP                      *
C   ***********************************************
C
520 DO 750 PNUM=1,NOP
C
C   ***********************************************
C   *  DISPLAY MANUAL CHECKLIST                   *
C   ***********************************************
C
        DO 525 J=1,31
525       WRITE (1,10)
        WRITE (1,530) PNUM,(PNAME(PNUM,J),J=1,30)
        WRITE (1,531)
        WRITE (1,532)
530     FORMAT(///
    +        ' PLACE PLATE #',I2,2X,30A1,' ON STAGE'//
    +        10X,' NOW    1. CHOOSE 10X OBJECTIVE '//
    +        10X,'        2. FOCUS ')
531     FORMAT(10X,'        3. CENTER THE FIRST WELL USING ',
    +                'ARROW KEYS AND RETICULE.'//
    +        10X,'        4. TURN BRIGHTFIELD LIGHT OFF'//
    +        10X,'        5. CHOOSE 16X FLUORESCENCE OBJECTIVE')
532     FORMAT(10X,'        6. PULL BEAM SPLITTER OUT'/
    +        10X,'        7. OPEN FLUORESCENCE FILTER SHUTTER'//
    +        '   ENTER "F" WHEN FINISHED       ')
C
        CALL STAGE
        READ  (1,540) JUNK
540     FORMAT(1A1)
```

```
365   C
366   C
367   C       ******************************************
368   C       *    ESTABLISH CONTROL RANGE             *
369   C       ******************************************
370
371   C       ******************************************
372   C       *    FIRST WELL - NEGATIVE CONTROL       *
373   C       ******************************************
374   C
375           CALL READPM( DFACT,GAVG,RAVG )
376           PDATA(1,1,1) = GAVG
377           PDATA(1,1,2) = RAVG
378   C
379   C       ******************************************
380   C       *    MOVE 1 WDIST +Y DIR (NEXT WELL)     *
381   C       ******************************************
382   C
383           X = 1
384           Y = 1
385           CALL ECHO( X,Y,GAVG,RAVG )
386           XDIST = WDIST(X,Y,1)
387           YDIST = WDIST(X,Y,2)
388           CALL NEXT( XDIST,YDIST )
389   C
390   C       ******************************************
391   C       *    SECOND WELL - POSITIVE CONTROL      *
392   C       ******************************************
393   C
394           CALL READPM( DFACT,GAVG,RAVG )
395           PDATA(1,2,1) = GAVG
396           PDATA(1,2,2) = RAVG
397   C
398           ******************************************
399           *    MOVE 1 WDIST IN +Y DIRECTION        *
400   C       ******************************************
401   C
402           X = 1
403           Y = 2
404           CALL ECHO( X,Y,GAVG,RAVG )
405           XDIST = WDIST(X,Y,1)
406           YDIST = WDIST(X,Y,2)
407           CALL NEXT( XDIST,YDIST )
408   C
409   C       ******************************************
410   C       *    ACCEPT OR REJECT CONTROL RANGE      *
411   C       ******************************************
412   C
413           TEMP=PDATA(1,1,1)/PDATA(1,1,2)-PDATA(1,2,1)/PDATA(1,2,2)
414           IF(TEMP.GT.0.5) GOTO 595
415           WRITE (1,590) PNUM
416   590     FORMAT(//'      CONTROL RATIO UNDER 0.5'/
417          +         '      FROM PLATE # ',I2)
418   595     CONTINUE
419   C
420   C       ******************************************
421   C       *    TRAVERSE DISK AND STORE RAW DATA    *
422   C       ******************************************
423   C
424           X = 1
425           Y = 3
426   C
427   600     IF(X.GE.XMAX) GOTO 700
428   610        IF(Y.GE.YMAX) GOTO 640
429              CALL READPM( DFACT,GAVG,RAVG )
430              PDATA( X,Y,1 ) = GAVG
431              PDATA( X,Y,2 ) = RAVG
432              CALL ECHO( X,Y,GAVG,RAVG )
433              XDIST = WDIST(X,Y,1)
434              YDIST = WDIST(X,Y,2)
435              CALL NEXT( XDIST,YDIST )
436              Y = Y+1
437              GOTO 610
438   640     CONTINUE
439   C
```

```
440             CALL READPM( DFACT,GAVG,RAVG )
441             PDATA( X,Y,1 ) = GAVG
442             PDATA( X,Y,2 ) = RAVG
443             CALL ECHO( X,Y,GAVG,RAVG )
444             XDIST = WDIST(X,Y,1)
445             YDIST = WDIST(X,Y,2)
446             CALL NEXT( XDIST,YDIST )
447             X = X+1
448     C
449       650   IF(Y.LE.1) GOTO 680
450             CALL READPM( DFACT,GAVG,RAVG )
451             PDATA( X,Y,1 ) = GAVG
452             PDATA( X,Y,2 ) = RAVG
453             CALL ECHO( X,Y,GAVG,RAVG )
454             XDIST = WDIST(X,Y,1)
455             YDIST = WDIST(X,Y,2)
456             CALL NEXT( XDIST,YDIST )
457             Y = Y-1
458             GOTO 650
459       680   CONTINUE
460     C
461             CALL READPM( DFACT,GAVG,RAVG )
462             PDATA( X,Y,1 ) = GAVG
463             PDATA( X,Y,2 ) = RAVG
464             CALL ECHO( X,Y,GAVG,RAVG )
465             XDIST = WDIST(X,Y,1)
466             YDIST = WDIST(X,Y,2)
467             CALL NEXT( XDIST,YDIST )
468             X = X+1
469             GOTO 600
470       700   CONTINUE
471     C
472     C
473     C       ****************************************
474     C       *   WRITE DATA TO DISK                 *
475     C       ****************************************
476             WRITE ( 8,710 ) (PNAME(PNUM,J),J=1,30)
477       710   FORMAT(30A1)
478             DO 740 X=1,XMAX
479               DO 730 Y=1,YMAX
480                 WRITE ( 8,715 ) PDATA(X,Y,1),PDATA(X,Y,2)
481       715       FORMAT(2F7.1)
482       730     CONTINUE
483       740   CONTINUE
484     C
485     C
486       750 CONTINUE
487     C
488     C
489     C       ****************************************
490     C       * ACKNOWLEDGE NORMAL PROGRAM TERMINATION *
491     C       ****************************************
492     C
493             DO 775 J=1,31
494       775   WRITE(1,10)
495             WRITE (1,777)
496       777 FORMAT(////
497             +   /'        *   FACT TERMINATES NORMALLY        *'
498             +   /'        ****************************************')
499     C
500     C
501             STOP
502             END
```

APPENDIX B

```
 1      C *************************************************
 2      C * THE PRINT PROGRAM PRINTS OUT THE DATA GATHERED *
 3      C * BY THE   DATA ACQUISITION PROGRAM              *
 4      C *************************************************
 5      C
 6              PROGRAM PRINT
 7      C
 8              INTEGER*1  NAME(30),FNAME(6),FILT,NOW
 9              INTEGER*1  RED(5),GREEN(5),FILTER(5)
10              INTEGER*1  DATE(15),OLINE(18)
11
12              INTEGER*1  OUT(12,10),NAMING,NUM(5,2)
13              INTEGER*1  TNAME(6),ABNAME(12,10,3),ABNOW
14              INTEGER*1  RREJ(12,10),GREJ(12,10),STAR
15              INTEGER*1  BLANK,RATREJ(12,10)
16      C
17      C
18              INTEGER*2  I,J,K,L,M,N
19              INTEGER*2  X,Y,Z,HV,GAIN
20              INTEGER*2  NOP,XEND,YEND
21
22              INTEGER*2  ABXEND,ABYEND
23              INTEGER*2  NORR,NOGR
24      C
25              REAL       LOR,HIR,HIG,LOG
26              REAL       GUP,GLOW,ZERO,HUND,RANGE,STEP
27              REAL       RUP,RLOW,ONE,TWO,THREE,FOUR
28              REAL       R(12,10),G(12,10),RATIO,RATDAT(12,10)
29              REAL       RSTDEV,GSTDEV,RAVG,GAVG
30      C
31              DATA       RED(1),RED(2),RED(3)/'R','E','D'/
32              DATA       GREEN(1),GREEN(2),GREEN(3)/'G','R','E'/
33              DATA       GREEN(4),GREEN(5)/'E','N'/
34              DATA       OLINE/18*0/
35              DATA       ABNAME/360*0/
36              DATA       BLANK /' '/
37              DATA       R,G /240*0.0/
38              DATA       OUT /120*0/
39              DATA       STAR /'*'/
40              DATA       NUM(1,1),NUM(2,1),NUM(3,1)/1,2,3/
41              DATA       NUM(4,1),NUM(5,1)          /4,5/
42              DATA       NUM(1,2),NUM(2,2),NUM(3,2)/1,2,4/
43              DATA       NUM(4,2),NUM(5,2)          /6,8/
44      C
45      C
46      C
47              WRITE (1,4)
48        4     FORMAT(///////////////////////////////
49             +         ' ENTER THE ANTIBODY FILE NAME : ')
50              READ   (1,5) (TNAME(J),J=1,6)
51        5     FORMAT(6A1)
52      C
53              WRITE (1,6)
54        6     FORMAT(///////////////////////////////
55             +         ' NOMENCLATURE DESIRED : 1.   1-5'/
56             +         '                        2.   1-8  ')
57              READ   (1,7) NAMING
58        7     FORMAT(I1)
59      C
60              CALL OPEN( 9,TNAME )
61              READ   (9,8) (TNAME(J),J=1,6)
62        8     FORMAT(6A1)
63              READ   (9,9) ABNOW,ABXEND,ABYEND
64        9     FORMAT(3I3)
65      C
66      C
67              CALL OPEN( 8,'1:FACT.DAT' )
68              READ   (8,10) NOP,XEND,YEND,GAIN,FILT,NOW,
69             +              (FNAME(J),J=1,6),HV,(DATE(K),K=1,15)
70       10     FORMAT(6I3,6A1,I4,15A1)
71      C
72              IF((NOW.NE.ABNOW).OR.(XEND.NE.ABXEND).OR.
```

```
73                  +                         (YEND.NE.ABYEND))    WRITE(2,11)
74            11  FORMAT(//1H+,' ANTIBODY TRAY DIMENSIONS DO NOT AGREE',
75                  +              ' WITH SAMPLE TRAY DIMENSIONS.'/1H+,
76                  +              ' CORRELATION OF AB NAMES AND RESULTS',
77                  +              ' MAY BE ERRONEOUS.')
78         C
79         C
80                  IF(FILT.EQ.1)  GOTO 15
81                     DO 13 J=1,5
82                        FILTER(J) = GREEN(J)
83            13     CONTINUE
84                  GOTO 17
85            15     DO 17 J=1,5
86                        FILTER(J) = RED(J)
87            17  CONTINUE
88         C
89                  GAIN = GAIN + 1
90                  GOTO (20,25,30,35), GAIN
91            20     GAIN = 1000
92                  GOTO 40
93            25     GAIN = 100
94                  GOTO 40
95            30     GAIN = 10
96                  GOTO 40
97            35     GAIN = 1
98            40  CONTINUE
99         C
100        C
101               WRITE (2,80)
102               WRITE (2,81)
103               WRITE (2,82) (DATE(J),J=1,15)
104               WRITE (2,83) NOP
105               WRITE (2,84) (FNAME(J),J=1,6),NOW
106               WRITE (2,86) HV
107               WRITE (2,88) GAIN
108               WRITE (2,90) (FILTER(J),J=1,5)
109               WRITE (2,92)
110               WRITE (2,94)
111        C
112           80  FORMAT(/2H+ ,'****************************',
113                 +              '****************************')
114           81  FORMAT(/2H+ ,'* THE FOLLOWING PARAMETERS APPLY',
115                 +              ' TO THIS PRINTOUT',12X,'*')
116           82  FORMAT(/2H+ ,'*            DATE OF PROCESSING :  ',
117                 +              15A1,13X,'*')
118           83  FORMAT(/2H+ ,'*  NUMBER OF PLATES PROCESSED :  ',
119                 +              I3,25X,'*')
120           84  FORMAT(/2H+ ,'*            TYPE OF PLATE USED :  ',
121                 +              6A1,I3,' WELL PLATE',8X,'*')
122           86  FORMAT(/2H+ ,'*            HIGH VOLTAGE :  ',
123                 +              I3,25X,'*')
124           88  FORMAT(/2H+ ,'*                        GAIN :  ',
125                 +              I3,25X,'*')
126           90  FORMAT(/2H+ ,'*            FIRST FILTER :  ',
127                 +              5A1,23X,'*')
128           92  FORMAT(/2H+ ,'****************************',
129                 +              '****************************')
130           94  FORMAT(/1H+)
131        C
132        C
133               DO 110 X=1,ABXEND
134                  DO 105 Y=1,ABYEND
135                     READ (9,100) (ABNAME(X,Y,J),J=1,3)
136          100       FORMAT(3I2)
137          105    CONTINUE
138          110  CONTINUE
139        C
140        C
141        C
142               DO 999 Z=1,NOP
143        C
144               READ (8,120) (NAME(J),J=1,30)
145          120  FORMAT(30A1)
146        C
147               NORR = 0
148               NOGR = 0
```

```
149               DO 130 X=1,XEND
150                 DO 125 Y=1,YEND
151                   RREJ(X,Y)  = BLANK
152                   GREJ(X,Y)  = BLANK
153                   RATREJ(X,Y) = BLANK
154                   RATDAT(X,Y) = 0.0
155        125     CONTINUE
156        130   CONTINUE
157     C
158               IF(FILT.EQ.1) GOTO 170
159                 DO 165 X=1,XEND
160                   DO 160 Y=1,YEND
161                     READ  (8,155) G(X,Y),R(X,Y)
162        155         FORMAT(2F7.1)
163                     IF( R(X,Y).GE.0.0 ) GOTO 157
164                       RREJ(X,Y) = STAR
165                       NORR      = NORR + 1
166        157         CONTINUE
167                     IF( G(X,Y).GE.0.0 ) GOTO 158
168                       GREJ(X,Y) = STAR
169                       NOGR      = NOGR + 1
170        158         CONTINUE
171        160       CONTINUE
172        165     CONTINUE
173               GOTO 200
174        170     DO 200 X=1,XEND
175                   DO 190 Y=1,YEND
176                     READ  (8,180) R(X,Y),G(X,Y)
177        180         FORMAT(2F7.1)
178                     IF( R(X,Y).GE.0.0 ) GOTO 184
179                       RREJ(X,Y) = STAR
180                       NORR      = NORR + 1
181        184         CONTINUE
182                     IF( G(X,Y).GE.0.0 ) GOTO 186
183                       GREJ(X,Y) = STAR
184                       NOGR      = NOGR + 1
185        186         CONTINUE
186        190       CONTINUE
187        200   CONTINUE
188     C
189     C
190     C     ***********************************************
191     C     *   CALCULATE RED AND GREEN AVERAGES          *
192     C     ***********************************************
193     C
194               RSTDEV = 0.0
195               GSTDEV = 0.0
196                RAVG  = 0.0
197                GAVG  = 0.0
198     C
199               CALL STATS( R, GREJ,XEND,YEND,RAVG,RSTDEV )
200               CALL STATS( G,RREJ,XEND,YEND,GAVG,GSTDEV )
201     C
202     C     ***********************************************
203     C     * DETERMINE WHICH VALUES ARE REJECTS          *
204     C     ***********************************************
205     C
206               GUP  = GAVG + 3*GSTDEV
207               GLOW = GAVG - 3*GSTDEV
208               RUP  = RAVG + 3*RSTDEV
209               RLOW = RAVG - 3*RSTDEV
210                 HIR=0.0
211                 HIG=0.0
212                 LOR=0.0
213                 LOG=0.0
214     C
215               DO 207 X=1,XEND
216                 DO 206 Y=1,YEND
217                   IF((R(X,Y).LE.RUP).AND.(R(X,Y).GE.RLOW)) GOTO 203
218                     RATREJ(X,Y)=STAR
219                     RREJ(X,Y) = STAR
220                     NORR = NORR + 1
221        203         IF((G(X,Y).LE.GUP).AND.(G(X,Y).GE.GLOW)) GOTO 204
222                     RATREJ(X,Y) = STAR
223                     GREJ(X,Y) = STAR
```

```
224                     NOGR = NOGR + 1
225                     GOTO 206
226       C
227       C *** FIND HIGHEST AND LOWEST GREEN & RED VALUE ***
228       C
229         204   IF (RREJ(X,Y).EQ.STAR) GOTO 206
230       C
231                     HIR = AMAX1(HIR,R(X,Y))
232                     LOR = AMIN1(LOR,R(X,Y))
233                     HIG = AMAX1(HIG,G(X,Y))
234                     LOG = AMIN1(LOG,G(X,Y))
235       C
236         206   CONTINUE
237         207   CONTINUE
238       C
239       C   ****************************************
240       C   * WRITE OUT PLATE HEADER               *
241       C   ****************************************
242       C
243               WRITE (2,310)
244               WRITE (2,315) Z
245               WRITE (2,320) (NAME(J),J=1,30)
246         310   FORMAT(////1H+)
247         315   FORMAT(/1H+,6X,'    PLATE NUMBER : ',I3)
248         320   FORMAT(/1H+,6X,'    PLATE NAME   : ',30A1/)
249       C
250               WRITE (2,330)
251               WRITE (2,340)
252         330   FORMAT(/10X,'A',9X,'B',9X,'C',9X,'D',9X,'E',9X,'F')
253         340   FORMAT(/1H+,3X,59('_'))
254       C
255       C
256       C   ****************************************
257       C   * WRITE OUT PLATE DATA                 *
258       C   ****************************************
259       C
260               DO 420 X=1,XEND,2
261                 WRITE (2,400) X,G(X,1),GREJ(X,1),
262              +                  G(X,2),GREJ(X,2),
263              +                  G(X,3),GREJ(X,3),
264              +                  G(X,4),GREJ(X,4),
265              +                  G(X,5),GREJ(X,5),
266              +                  G(X,6),GREJ(X,6)
267                 WRITE (2,410)   R(X,1),RREJ(X,1),
268              +                  R(X,2),RREJ(X,2),
269              +                  R(X,3),RREJ(X,3),
270              +                  R(X,4),RREJ(X,4),
271              +                  R(X,5),RREJ(X,5),
272              +                  R(X,6),RREJ(X,6)
273                 Y = X+1
274                 WRITE (2,400) Y,G(Y,6),GREJ(Y,6),
275              +                  G(Y,5),GREJ(Y,5),
276              +                  G(Y,4),GREJ(Y,4),
277              +                  G(Y,3),GREJ(Y,3),
278              +                  G(Y,2),GREJ(Y,2),
279              +                  G(Y,1),GREJ(Y,1)
280                 WRITE (2,410)   R(Y,6),RREJ(Y,6),
281              +                  R(Y,5),RREJ(Y,5),
282              +                  R(Y,4),RREJ(Y,4),
283              +                  R(Y,3),RREJ(Y,3),
284              +                  R(Y,2),RREJ(Y,2),
285              +                  R(Y,1),RREJ(Y,1)
286         400   FORMAT(/1H+,I2,1X,'|',6(F7.1,A1,2X))
287         410   FORMAT(/1H+,3X,'|',6(F7.1,A1,2X))
288         420   CONTINUE
289       C
290               WRITE (2,425) GAVG,GSTDEV
291               WRITE (2,430) RAVG,RSTDEV
292         425   FORMAT(/1H+,' AVERAGE GREEN VALUE = ',F7.2,
293              +                  ' +/- ',F7.2)
294         430   FORMAT(/1H+,' AVERAGE RED   VALUE = ',F7.2,
295              +                  ' +/- ',F7.2)
296       C
297               WRITE (2,433) HIG
298               WRITE (2,435) LOG
```

```
299              WRITE (2,437) HIR
300              WRITE (2,439) LOR
301        433   FORMAT(/1H+,'  HIGH GREEN VALUE = ',F7.2)
302        435   FORMAT(/1H+,'  LOW  GREEN VALUE = ',F7.2)
303        437   FORMAT(/1H+,'  HIGH RED   VALUE = ',F7.2)
304        439   FORMAT(/1H+,'  LOW  RED   VALUE = ',F7.2)
305   C
306   C         ************************************************
307   C         * CALCULATE ADJUSTED AVERAGES                  *
308   C         ************************************************
309   C
310              CALL STATS( G,GREJ,XEND,YEND,GAVG,GSTDEV )
311   C
312              WRITE (2,471)
313              WRITE (2,472) NOGR
314              WRITE (2,425) GAVG,GSTDEV
315        471   FORMAT(/1H+,'  ADJUSTED AVERAGE(S) : ')
316        472   FORMAT(/1H+,'  NUMBER OF REJECTED GREEN',
317           +              '  VALUES = ',I3)
318   C
319              CALL STATS(R,RREJ,XEND,YEND,RAVG,RSTDEV )
320   C
321              WRITE (2,485) NORR
322              WRITE (2,430) RAVG,RSTDEV
323        485   FORMAT(/1H+,'  NUMBER OF REJECTED RED   ',
324           +              '  VALUES = ',I3)
325   C
326              HIRAT = 0.0
327              LORAT =  99999.9
328   C
329              DO 495 X=1,XEND
330                 DO 490 Y=1,YEND
331   C
332                 IF(RATREJ(X,Y).EQ.STAR) GOTO 490
333   C
334                    RATDAT(X,Y) = G(X,Y)/R(X,Y)
335                    HIRAT = AMAX1(RATDAT(X,Y),HIRAT)
336                    LORAT = AMIN1(RATDAT(X,Y),LORAT)
337        490     CONTINUE
338        495   CONTINUE
339   C
340              GUP  = G( 1,1 )
341        500   GLOW = G( 1,2 )
342   C
343              RUP  = R( 1,2 )
344              RLOW = R( 1,1 )
345   C
346              ZERO = GUP/RLOW
347              HUND = GLOW/RUP
348   C
349              IF ((ZERO.LT.HUND).OR.((ZERO-HUND).GT.0.5)) GOTO 510
350                 ZERO = HIRAT
351                 HUND = LORAT
352   C
353        510   RANGE = ZERO - HUND
354              STEP  = RANGE/5
355   C
356   C
357   C
358   C         ************************************************
359   C         * CALCULATE & STORE   STEPS                    *
360   C         ************************************************
361   C
362              ONE   = ZERO-STEP
363              TWO   = ZERO-(2*STEP)
364              THREE = ZERO-(3*STEP)
365              FOUR  = ZERO-(4*STEP)
366   C
367   C
368              DO 600 X=1,XEND
369                 DO 590 Y=1,YEND
370   C
371                    RATIO = RATDAT(X,Y)
372   C
```

```
373            IF (RATIO.GE.ONE)        OUT(X,Y)=NUM(1,NAMING)
374    C
375            IF((RATIO.LT.ONE).AND.
376          +     (RATIO.GE.TWO))       OUT(X,Y)=NUM(2,NAMING)
377    C
378            IF((RATIO.LT.TWO).AND.
379          +     (RATIO.GE.THREE))     OUT(X,Y)=NUM(3,NAMING)
380    C
381            IF((RATIO.LT.THREE).AND.
382          +     (RATIO.GE.FOUR))      OUT(X,Y)=NUM(4,NAMING)
383    C
384            IF (RATIO.LT.FOUR)        OUT(X,Y)=NUM(5,NAMING)
385    C
386    C
387       590  CONTINUE
388       600 CONTINUE
389    C
390    C     ************************************
391    C     * REUSE GAVG/GSTDEV FOR RATIOS     *
392    C     ************************************
393    C
394            GAVG = 0.0
395            GSTDEV = 0.0
396            CALL STATS( RATDAT,RATREJ,XEND,YEND,GAVG,GSTDEV )
397    C
398    C     ************************************************
399    C     * REJECT RATIOS >3 STD DEV FROM MEAN           *
400    C     * REUSE GUP/GLOW FOR RATIOS                    *
401    C     ************************************************
402    C
403            GUP  = GAVG + 3*GSTDEV
404            GLOW = GAVG - 3*GSTDEV
405    C
406            DO 607 X=1,XEND
407              DO 606 Y=1,YEND
408                IF( (RATDAT(X,Y).GT.GUP).OR.
409          +         (RATDAT(X,Y).LT.GLOW) )
410          +          RATREJ(X,Y) = STAR
411       606  CONTINUE
412       607 CONTINUE
413    C
414    C
415    C
416            WRITE (2,620)
417            WRITE (2,620)
418    C
419    C     ************************************************
420    C     * WRITE OUT RATIO DATA (RATDAT)                *
421    C     ************************************************
422    C
423            DO 615 M=1,XEND,2
424              X = M
425              WRITE (2,610) X,RATDAT(X,1),RATREJ(X,1),
426          +                   RATDAT(X,2),RATREJ(X,2),
427          +                   RATDAT(X,3),RATREJ(X,3),
428          +                   RATDAT(X,4),RATREJ(X,4),
429          +                   RATDAT(X,5),RATREJ(X,5),
430          +                   RATDAT(X,6),RATREJ(X,6)
431              X = X+1
432              WRITE (2,610) X,RATDAT(X,6),RATREJ(X,6),
433          +                   RATDAT(X,5),RATREJ(X,5),
434          +                   RATDAT(X,4),RATREJ(X,4),
435          +                   RATDAT(X,3),RATREJ(X,3),
436          +                   RATDAT(X,2),RATREJ(X,2),
437          +                   RATDAT(X,1),RATREJ(X,1)
438       610  FORMAT(/1H+,I6,' ',6(F7.3,A1))
439       615 CONTINUE
440    C
441            WRITE (2,618) GAVG,GSTDEV
442       618  FORMAT(/1H+,' AVERAGE RATIO = ',F7.2,
443          +         ' +/- ',F7.2)
444    C
445    C
```

```
C     ******************************************
C     *      WRITE OUT REDUCED DATA    (OUT)   *
C     ******************************************
C
      WRITE (2,620)
      WRITE (2,620)
  620 FORMAT(/1H+)
C
C
C
      WRITE (2,622)
  622 FORMAT(/1H+,11X,'A',8X,'B',8X,'C',8X,'D',8X,'E',8X,'F')
      WRITE (2,720)
C
      DO 750 M=1,XEND,2
C
         X = M
C
         DO 625 J=1,18
            OLINE(J) = 0
  625    CONTINUE
C
         N = 1
         DO 640 Y=1,ABYEND
            DO 635 J=1,3
               OLINE(N) = ABNAME(X,Y,J)
               N = N+1
  635       CONTINUE
  640    CONTINUE
C
         WRITE (2,740) (OLINE(J),J=1,18)
C
         WRITE (2,730)X,OUT(X,1),OUT(X,2),OUT(X,3),
     +                  OUT(X,4),OUT(X,5),OUT(X,6)
         WRITE (2,720)
C
         X = X+1
C
         DO 650 J=1,18
            OLINE(J) = 0
  650    CONTINUE
C
         N = 1
         DO 660 Y=1,ABYEND
            DO 655 J=1,3
               K = ABYEND-Y+1
               OLINE(N) = ABNAME(X,K,J)
               N = N+1
  655       CONTINUE
  660    CONTINUE
C
C
         WRITE (2,740) (OLINE(J),J=1,18)
C
         WRITE (2,730)X,OUT(X,6),OUT(X,5),OUT(X,4),
     +                  OUT(X,3),OUT(X,2),OUT(X,1)
         WRITE (2,720)
C
  720    FORMAT(/1H+,6X,55('-'))
  730    FORMAT(/1H+,I6,'|',I8,'|',5(I8,'|'))
  740    FORMAT(/1H+,6X,'|',6(I2,',',I2,',',I2,'|'))
  750 CONTINUE
C
  999 CONTINUE
C
      WRITE (1,2000)
      WRITE (1,2001)
      WRITE (1,2002)
C
 2000 FORMAT(////////////////////////////////
     +          *********************************')
 2001 FORMAT('   *    PRINTR TERMINATES NORMALLY        *')
 2002 FORMAT('   *********************************')
C
C
```

We claim:

1. For use in fluorescence assays of specimens exhibiting fluorescence at two distinguishable wavelength bands when irradiated respectively by light of two preselected distinguishable wavelength bands; apparatus comprising:

a movable specimen container having spaced compartments for a plurality of individual specimens to be assayed;

alignment means for moving the container to provide predetermined sequential centered alignment of individual compartments of the container with a predetermined optical path;

irradiating means for sequentially irradiating said specimens, as each is aligned in the optical path, alternately with light of the two pre-selected distinguishable wavelength bands beamed along the optical path;

light collection means for receiving and distinguishing light produced by fluorescence in each said specimen along the optical path;

detector means for detecting and recording the intensity of the light produced by fluorescence of each said specimen at each of said two distinguishable wavelength bands;

analyzing means for calculating the quotient of the intensities of the light sequentially received from each said specimen at the two distinguishable wavelength bands and for comparing such quotient with at least one control quotient thereby to classify such specimen according to such comparison; and synchronization means for controlling, coordinating and synchronizing the operation of the alignment means, irradiating means, light collection means, detector means and analyzing means.

2. Apparatus as defined in claim 1, wherein the synchronization means comprises a computer programmed to control, coordinate and synchronize the operation of the alignment means, irradiating means, light collection means, detector means, and analyzing means.

3. Apparatus as defined in claim 2, wherein the analyzing means is part of the computer.

4. Apparatus as defined in claim 1, wherein the light collection means includes a pair of barrier filters each alternately selectable to pass light of a respective one of said two distinguishable wavelength bands to the detector means.

5. Automated apparatus for observing fluorescence stimulated by a light source in a plurality of specimens in a transparent specimen holder containing said specimens in a planar array, each of said specimens exhibiting fluorescence at a first emission wavelength when irradiated with light of a first exciting wavelength and fluorescence at a second emission wavelength when irradiated with light of a second exciting wavelength, comprising:

(i) an inversion microscope including a scanning stage operable to retain said specimen holder and to be sequentially positioned to place each of said specimens sequentially at a selected centered position within the objective field of such microscope to collect for observation fluorescent radiation from such specimen;

(ii) power means operable to drive said scanning stage in orthogonal directions within a plane perpendicular to the focal axis of the objective of said microscope;

(iii) first and second optical systems operable when said first and second optical systems are respectively positioned in the path of light from said source, to direct sequentially light of said first incident wavelength and said second incident wavelength, sequentially to the specimen located at said selected position, and to transmit light of said first emission wavelength and said second emission wavelength, respectively, from said specimen located at said selected position to the ocular of said microscope for observation;

(iv) motorized means for alternately positioning said first optical system and said second optical system in the path of light from said source; and (v) control means operatively connected with each of said power means and said motorized means for moving said scanning stage in incremental steps to place each of said specimens sequentially at said selected position within the objective field of said microscope for a predetermined period of time and to actuate said motorized slide means during said predetermined period of time so that fluorescence light of said first emission wave length and of said second emission wave length is observed by means of said microscope for each of said specimens;

(vi) photodetector means coupled with said microscope and operable to produce an amplified signal proportional to the intensity of radiation emitted by a sample located at the selected position within the optical field of said microscope; and (vii) a computer programmed to collect and store signal data from said photodetector measuring the fluorescence light intensity at said first emission wavelength and at said second emission wavelength from each said sample, and to transform said data into quotients which are directly related to reference data for positive and negative control standards of a given double-stained sample, said computer being programmed to coordinate said control means so that each said specimen is successively placed within the optical field of said microscope where it is alternatively irradiated with light of said first and second incident wavelengths.

6. Apparatus according to claim 5, wherein said first and second optical systems are epi-fluorescence condenser sets and said motorized slide means comprises (i) a housing to hold said epi-fluorescence condenser sets in parallel side-by-side alignment, said housing being axially movable between two stop positions to alternately place said epi-fluorescence condenser sets in the path of light from said source, and (ii) a motor operatively connected to said housing for moving said housing between said two stop positions.

7. Apparatus according to claim 6, wherein said specimen holder is a tray having identical U-shaped, flat bottom or round bottom wells therein for holding specimens in a rectangular array of rows and columns.

8. Apparatus according to claim 7, wherein said power means and said control means are operable to place each of said identical wells sequentially at said selected position within the objective field of said microscope so that each of the wells is centered within the optical field of said microscope when fluorescence from said well is being observed.

9. Automated apparatus for the photometric analysis of a plurality of specimens of cellular material, each such specimen having been stained with a first fluorochrome exhibiting fluorescence at a first emission wavelength when irradiated with light at a first incident wavelength and a second fluorochrome exhibiting fluorescence at a second emission wavelength contrasting with first emission wavelength when irradiated with light at a second incident wavelength, comprising:

(i) a microtest tray operable to hold said specimens and appropriate fluorescence control standards within an array of discrete wells;

(ii) an inverted epi-fluorescence microscope, comprising:

(a) a motorized scanning stage operable to retain said microtest tray and to be sequentially positioned to place each of said wells sequentially at a selected centered position within the optical field of said microscope to collect fluorescent radiation from the specimen in said well, (b) first control means operatively connected with said motorized scanning stage for moving said scanning stage in incremental steps to place each of said wells sequentially at said selected position, (c) a light source operable to irradiate any of said specimens located at said selected position within the optical field of the microscope, (d) first and second epi-fluorescence condenser sets operable to admit light of said first incident wavelength and said second incident wavelength, respectively, and to be interposed between said light source and said specimen located at said selected position within the optical field of the microscope, (e) motorized filter-changing means operable to alternate the interposition of said first condenser set and said second condenser set between said light source and said specimen, (f) second control means operatively connected with said motorized filter-changing means for successively irradiating each sample located at said selected position in the optical field of said microscope first with light of said first incident wavelength and then with light of said second incident wavelength for predetermined intervals of time;

(iii) photodetector means coupled with said microscope and operable to produce an amplified signal proportional to the intensity of radiation emitted by a sample located at the selected position within the optical field of said microscope;

(iv) a computer programmed to collect and store signal data from said photodetector measuring the fluorescence light intensity at said first emission wavelength and at said second emission wavelength from each said sample, and to transform said data into quotients which are directly related to reference data for positive and negative control standards of a given double-stained sample, said computer being programmed to coordinate said first control means and said second control means so that each said specimen is successively placed within the optical field of said microscope where it is alternatively irradiated with light of said first and second incident wavelengths.

10. Apparatus according to claim 9, wherein said specimens comprise mixtures of live and dead cells in unknown proportions and a number of positive and negative control standards having majority proportions of live or dead cells, respectively, and wherein said computer is programmed to transform original intensity fluorescence data into quotients directly related to reference intensity fluorescence data for said positive and negative control standards and to compute and display data expressed as the percentage of live and dead cells in each said sample.

11. For use in fluorescence assays of specimens of cellular material exhibiting fluorescence at two distinguishable wavelength bands when irradiated respectively by light of two pre-selected distinguishable wavelength bands; an automated method comprising:
selecting and ordering specimens containing substantially uniform quantities of cellular material;
sequentially aligning individual ones of said specimens with an optical path;
irradiating the specimens sequentially and alternately with light of the two pre-selected distinguishable wavelength bands beamed along the optical path;
receiving and distinguishing light produced by fluorescence caused by the sequential and alternate irradiation of each said specimen along the optical path; and
detecting the intensity of the light produced by fluorescence of each said specimen at each of said two distinguishable wavelength bands;
calculating the quotient of the intensities of the light sequentially received from each said specimen at the two distinguishable wavelength bands; and
comparing the said quotient for each specimen against a predetermined control quotient thereby to classify the specimen according to such comparison;
said method including automatically synchronizing and coordinating all of the foregoing steps other than the selection and ordering of specimens.

12. The method of claim 11, wherein the specimens are selected for IF measurement of the cytotoxic reaction between prepared lymphocytes and selected identical quantities of antisera, and wherein the specimens are prepared according to the following sequential steps:
(a) adding the washed lymphocytes to a first staining solution to prepare a suspension having a known concentration of lymphocytes, said first staining solution comprising a first fluorochrome selectively staining living cells,
(b) adding a selected quantity of said suspension to each of said antisera and immediately thereafter adding to each of the antiserum-lymphocyte specimens a selected quantity of complement,
(c) agitating the specimens at room temperature for a selected period of time,
(d) adding to each of the specimens a selected quantity of a second staining solution comprising a second fluorochrome selectively staining dead cells and exhibiting fluorescence over a range of wavelengths contrasting with the range of fluorescence exhibited by said first fluorochrome, and
(e) incubating the specimens for a selected period of time.

13. A method as defined in claim 12, comprising the additional step:
(f) adding to each of the incubated specimens a stabilizer to inhibit further cytotoxic reaction between the antibodies of said antisera and the antigens of said lymphocytes.

14. A method as defined in claim 13, wherein said first fluorochrome is selected from the group consisting of fluorescein diacetate, fluorescein isothiocyanate and carboxyfluorescein diacetate.

15. A method as defined in claim 13 or claim 14, wherein said second stain is selected from the group consisting of ethidium bromide, propidium iodide, rhodamine and rhodamine isothiocyanate.

16. A method as defined in claim 12 or 13, wherein the lymphocytes are washed in a non-autofluorescing wash solution before they are added to the first staining solution.

17. A method as defined in claim 13, wherein said first fluorochrome is fluorescein diacetate and said second fluorochrome is ethidium bromide.

18. A method as defined in claim 17, wherein said first staining solution comprises acetone and fluorescein diacetate having a stock concentration lying in the range 3-6 mg fluorescein diacetate per ml of acetone and said second staining solution contains 1 $\mu$g of ethidium bromide per 1 ml of Veronal buffer having a pH of 7.0.

19. A method as defined in claim 18, wherein the final concentration of the first staining solution is of the order of 50 ng per $\mu$l acetone/HBSS/BSA mixture per $2 \times 10^6$ cells.

20. A method as defined in claim 19, wherein said selected quantity of said suspension added to said antisera contains a known quantity of lymphocytes lying in the range of $1.5 \times 10^3$ to $3.0 \times 10^3$ per $\mu$l of antiserum for each of said antisera.

21. A method as defined in claim 20, wherein said complement is rabbit C' and said selected quantity of complement lies in the range of 1-2 $\mu$l per $\mu$l of antiserum.

22. A method as defined in claim 21, wherein said agitation of antiserum-lymphocyte-complement specimens at room temperature is effected by agitation of the specimens at a rate of 10-50 cycles per minute for a period of 30-80 minutes.

23. A method as defined in claim 22, wherein subsequent to the addition of said second staining solution to said specimens the specimens are incubated for a period of time lying in the range of 7-15 minutes.

24. A method as defined in claim 21, claim 22, or claim 23, wherein said stabilizer is EDTA-NaCl solution having a concentration lying in the range of 0.2 to 1.2%.

* * * * *